(12) United States Patent
Woolson (10) Patent No.: US 11,007,104 B2
(45) Date of Patent: May 18, 2021

(54) FRAME AND METHOD FOR POSITIONING A PATIENT UNDERGOING HIP SURGERY

(71) Applicant: Steven T. Woolson, Palo Alto, CA (US)

(72) Inventor: Steven T. Woolson, Palo Alto, CA (US)

(*) Notice: Subject to any disclaimer, the term of this patent is extended or adjusted under 35 U.S.C. 154(b) by 469 days.

(21) Appl. No.: 16/101,229

(22) Filed: Aug. 10, 2018

(65) Prior Publication Data

US 2019/0053965 A1 Feb. 21, 2019

Related U.S. Application Data

(60) Provisional application No. 62/546,980, filed on Aug. 17, 2017.

(51) Int. Cl.
*A61G 13/12* (2006.01)
*A61G 13/00* (2006.01)
*A61F 5/37* (2006.01)

(52) U.S. Cl.
CPC ........ *A61G 13/0081* (2016.11); *A61F 5/3769* (2013.01); *A61G 13/123* (2013.01); *A61G 13/1295* (2013.01); *A61G 2200/32* (2013.01)

(58) Field of Classification Search
CPC ............ A61G 13/0081; A61G 13/0036; A61G 13/12; A61G 13/1205; A61G 13/123; A61G 13/128; A61G 13/1295; A61F 5/3769; A61F 5/37
USPC .......................................... 5/624, 621, 648
See application file for complete search history.

(56) References Cited

U.S. PATENT DOCUMENTS

| | | | |
|---|---|---|---|
| 3,823,709 A * | 7/1974 | McGuire | A61G 13/0072 600/230 |
| 3,844,550 A | 10/1974 | McGuire et al. | |
| 5,040,546 A | 8/1991 | Deluhery et al. | |
| 5,390,383 A | 2/1995 | Carn et al. | |
| 5,484,393 A * | 1/1996 | McCoy | A61F 5/02 5/621 |
| 6,003,176 A | 12/1999 | Wasley et al. | |
| 6,298,507 B1 * | 10/2001 | Clyburn | A61G 13/12 248/445 |
| 6,311,349 B1 * | 11/2001 | Kazakia | A61G 13/12 128/845 |
| 6,564,406 B2 | 5/2003 | Vansteenburg et al. | |
| 6,622,324 B2 * | 9/2003 | VanSteenburg | A61G 13/04 128/845 |
| 6,820,621 B2 | 11/2004 | Demayo et al. | |
| 8,118,029 B2 * | 2/2012 | Gneiting | A61G 13/0081 128/845 |
| 8,443,473 B2 | 5/2013 | Maxwell et al. | |
| 8,905,035 B2 | 12/2014 | Wilson et al. | |
| 9,226,865 B2 | 1/2016 | Jackson et al. | |

(Continued)

*Primary Examiner* — Robert G Santos
(74) *Attorney, Agent, or Firm* — Wilson Sonsini Goodrich & Rosati (57) ABSTRACT

The patient positioning frame includes a posterior support, a lateral support, and an anterior restraint. The patient positioning frame can be placed on an upper surface of a conventional surgical table with the posterior support lying horizontally and the lateral support position vertically. A patient lies supine on the lateral support and is restrained using the anterior restraint assembly. The patient and the patient support are then simultaneously turned on the table to expose the patient's hip region for subsequent hip replacement or other surgery.

23 Claims, 9 Drawing Sheets

(56) References Cited

U.S. PATENT DOCUMENTS

| | | | |
|---|---|---|---|
| 9,554,959 B2 * | 1/2017 | Carn | A61G 13/123 |
| 9,636,266 B2 | 5/2017 | Jackson et al. | |
| 2002/0157186 A1 * | 10/2002 | VanSteenburg | A61G 13/0081 |
| | | | 5/621 |
| 2003/0178027 A1 * | 9/2003 | DeMayo | A61G 13/0081 |
| | | | 128/845 |
| 2009/0044813 A1 * | 2/2009 | Gneiting | A61G 13/12 |
| | | | 128/845 |
| 2014/0059773 A1 * | 3/2014 | Carn | A61G 13/123 |
| | | | 5/624 |
| 2018/0243148 A1 * | 8/2018 | Iwakiri | A61B 17/56 |
| 2018/0256428 A1 * | 9/2018 | Blackwell | A61G 13/1295 |
| 2018/0256429 A1 * | 9/2018 | Blackwell | A61G 13/1285 |
| 2019/0053965 A1 * | 2/2019 | Woolson | A61G 13/1295 |

\* cited by examiner

FRAME AND METHOD FOR POSITIONING A PATIENT UNDERGOING HIP SURGERY

CROSS-REFERENCE TO RELATED APPLICATIONS

This application claims the benefit of U.S. Provisional No. 62/546,980, filed Aug. 17, 2017, the entire content of which is incorporated herein by reference.

BACKGROUND OF THE INVENTION

1. Field of the Invention

The present invention relates generally to medical devices and methods. More particularly, the invention relates to a patient support frame and a procedure for using the patient support frame to position a patient on a surgical table for performing total hip replacement and other hip surgeries.

Total hip replacement (THR) is a common surgery used to treat hip failure by replacing the patient's femoral head and acetabular cup with prosthetic components. THR surgery requires separation of the patient's femur from the hip and access to the exposed anatomies to perform the bone removals and subsequent prosthetic implantations.

While a variety of protocols involving different patient positions have been proposed over the years, most commonly the patient is positioned on his or her non-operative side and the surgery performed with a lateral approach. Typically, the patient is placed in a frame which is incorporated into or previously attached to an operating table and the patient strapped or clamp into the frame. It is frequently difficult to properly position the patient, and such frames often have a superstructure which can limit access to the target anatomies during a THR or other hip surgery.

For these reasons, it would be desirable to provide improved patient support frames and procedures for positioning a patient on a surgical table for performing total hip replacement and other hip surgeries. In particular, it would be desirable that such improved frames and procedures would simplify initial positioning of the patient and provide for optimum positioning of the patient during subsequent surgery. It would be further desirable that such improved frames and procedures would limit and reduce the presence of brackets, clamps, and other hardware that could potentially interfere with performance of the THR or other procedure. At least some of these objectives will be met by the inventions described below.

2. Description of the Background Art

Positioners and support devices for use in total hip replacement of other surgical procedures are described in U.S. Pat. Nos. 3,844,550; 5,040,546; 5,390,383; 6,003,176; and 6,820,621. Other pertinent patents include U.S. Pat. Nos. 9,636,266; 9,226,865; 8,905,035; 8,443,473; and 6,564,406.

SUMMARY OF THE INVENTION

The present invention provides improved apparatus and methods for positioning patients prior to surgery, particularly prior to total hip replacement (THR) and other surgical procedures on or near the hip joint. The invention herein allows for the patient to be initially placed on a positioning frame while the patient lies supine on top of a normal surgical table. Particularly, the surgical table does not need to be modified or enhanced in any way for use with the apparatus and in the methods of the present invention.

After the patient lies supine on the positioning frame, the patient is secured to the frame, typically using an anterior restraint, and the patient and the positioning frame can be simultaneously turned to place the patient on his or her side to expose the hip or other target surgical region. The positioning frame is free from structure which, after the patient has been repositioned, would interfere with the procedure to be performed. In some instances, portions of the positioning frame can be removed after the patient has been turned to even further enhance access to the surgical site.

In a first aspect, the present invention provides a patient positioning frame comprising a posterior support, a lateral support, and an anterior restraint. The posterior support and the lateral support are generally planar structures, and the lateral support is typically attached orthogonally to the posterior support so that they form an L-shaped frame or scaffold. The anterior restraint is adjustably coupled to the lateral support and is configured to engage a hip region of a patient to immobilize the hip region relative to the posterior and lateral supports of the positioning frame. By using the positioning frame, the patient can lie supine with his or her back against the posterior support while the posterior support is in a horizontal position relative to the surgical table. After the patient is positioned on the posterior support, the anterior restraint can be adjusted relative to the lateral support to immobilize the patient's hip region relative to the positioning frame. In this way, the patient and patient positioning frame can be simultaneously turned so that the lateral support lies horizontally on the surgical table, and the posterior support and the patient's pelvis are oriented vertically.

In specific aspects of the present invention, the posterior support may comprise (1) a backboard having an inner edge fixed to an inner edge of the lateral support and (2) an extension having an inner edge removably secured to an outer edge of the backboard. As described in more detail below, having a removable extension allows the posterior support to be partially dismantled after the patient has been reoriented and the need for support from the posterior support is reduced. In other embodiments, the posterior support may further comprise (3) a sacral post which extends from the outer edge of the backboard such that the sacral post will engage a patient's sacrum when the patient's back is engaged against the posterior support and the patient's side is engaged against the lateral support. In some instances, the sacral post may be configured to be repositioned along a length of the outer edge of the backboard in order to accommodate different patient anatomies. In addition, repositioning of the sacral post will allow the posterior support to be configured to treat patients lying on either their right side or their left side.

In still further instances, the posterior support and/or the lateral support may be provided with handles to allow manual repositioning of the patient positioning frame. This is a particular advantage as the patient together with the frame will usually be manually repositioned after the patient has been secured to the frame. Typically, the handles in or on the lateral support may be separated by a gap, and the anterior restraint may be coupled to the lateral support within the gap. In still further specific instances, the handles on the lateral support may be located at the outer ends of wings which extend from the lateral support. The presence of these wings, located on either side of the anterior restraint, provide additional leverage to allow the users to turn and reposition the patient while secured to the frame.

In still further specific instances, the anterior restraint of the patient positioning frame of the present invention may comprise (1) a post having an anterior and a posterior end. The restraint may further comprise a (2) cantilevered section extending laterally from the anterior end of the post. Typically, the posterior end of the post is translatably attached to the lateral support so that a spacing between the cantilevered section and the posterior support can be adjusted to accommodate different patient anatomies. Optionally, the anterior restraint may further comprise (3) a plurality of hip-engaging pads which extend in a posterior direction to engage the pelvis of the patient when the patient is lying supine on the posterior support with the cantilevered section extending over the pelvis. At least some of the plurality of hip-engaging pads will typically be configured to be adjustably positioned in an anterior/posterior direction relative to the cantilevered section. In still further instances, the anterior restraint may comprise or be paired with a chest bar extending laterally from the lateral support to lie over the patient's chest when the patient is lying supine on the posterior support. Typically, the chest bar will be repositionable on the lateral support to accommodate different patient anatomies.

In a second aspect, the present invention provides a method for positioning a patient for a surgical procedure. The method comprises providing a patient positioning frame which includes a posterior support attached orthogonally to a lateral support. The posterior support of the positioning frame is placed in a first horizontal orientation on an upper surface of the surgical table so that the lateral support extends vertically upwardly from the upper surface. The patient may thus be secured in a supine position over the posterior support of the positioning frame with the non-operative side of the patient adjacent to the lateral support while the patient positioning frame remains in the first orientation. The patient positioning frame and the patient can then be simultaneously turned to a second orientation on the lateral support to lie horizontally on the upper surface of the surgical table where the posterior support extends vertically upwardly from the upper surface. In this position, the desired side of the patient is exposed for a surgical procedure or other purposes. The methods of the present invention are particularly useful for performing surgery on the patient's hip region, more specifically for performing total hip replacement.

In specific aspects of the methods of the present invention, securing the patient in a supine position comprises engaging an anterior restraint against the pelvis of the patient. The anterior restraint is typically adjustably coupled to the lateral support, and engaging a lateral support against the hip region may comprise repositioning the anterior restraint relative to the lateral support. Repositioning the anterior restraint may further comprise repositioning a plurality of hip-engaging pads which extend in an anterior-posterior direction to engage the hip region of the patient.

In other specific aspects of the methods of the present invention, access to the target patient anatomy may be improved by removing an upper portion, referred to as an extension, of the posterior support after the patient and patient positioning frame have been turned to expose a surgical target region. In specific instances, removing the extension of the posterior support leaves a sacral post extending upwardly from the remaining portion of the posterior support to engage the patient's sacrum. Use of the sacral post is an advantage as it stabilizes the patient while exposing regions of the hip on either side of the post. Often, the sacral post will be repositionable along an edge of the posterior support before or after the upper portion of the support has been removed.

Methods of the present invention are particularly advantageous as they allow for manual repositioning of the patient while assuring that the patient is in a precisely selected orientation and is stably maintained within that orientation. The methods and devices of the present invention are also suitable for reconfiguring to accommodate both a right side and a left side of the patient prior to securing the patient to the patient positioning frame by orienting the positioning frame in the opposite direction than that depicted. While particularly intended for manual repositioning, it will be appreciated that the positioning frames and patients could be turned using hoists or other mechanical assistance if necessary.

BRIEF DESCRIPTION OF THE DRAWINGS

Various aspects of the invention will become clear from the following description of an illustrative embodiment and from the attached drawings, in which.

DETAILED DESCRIPTION OF THE INVENTION

Figure 1:
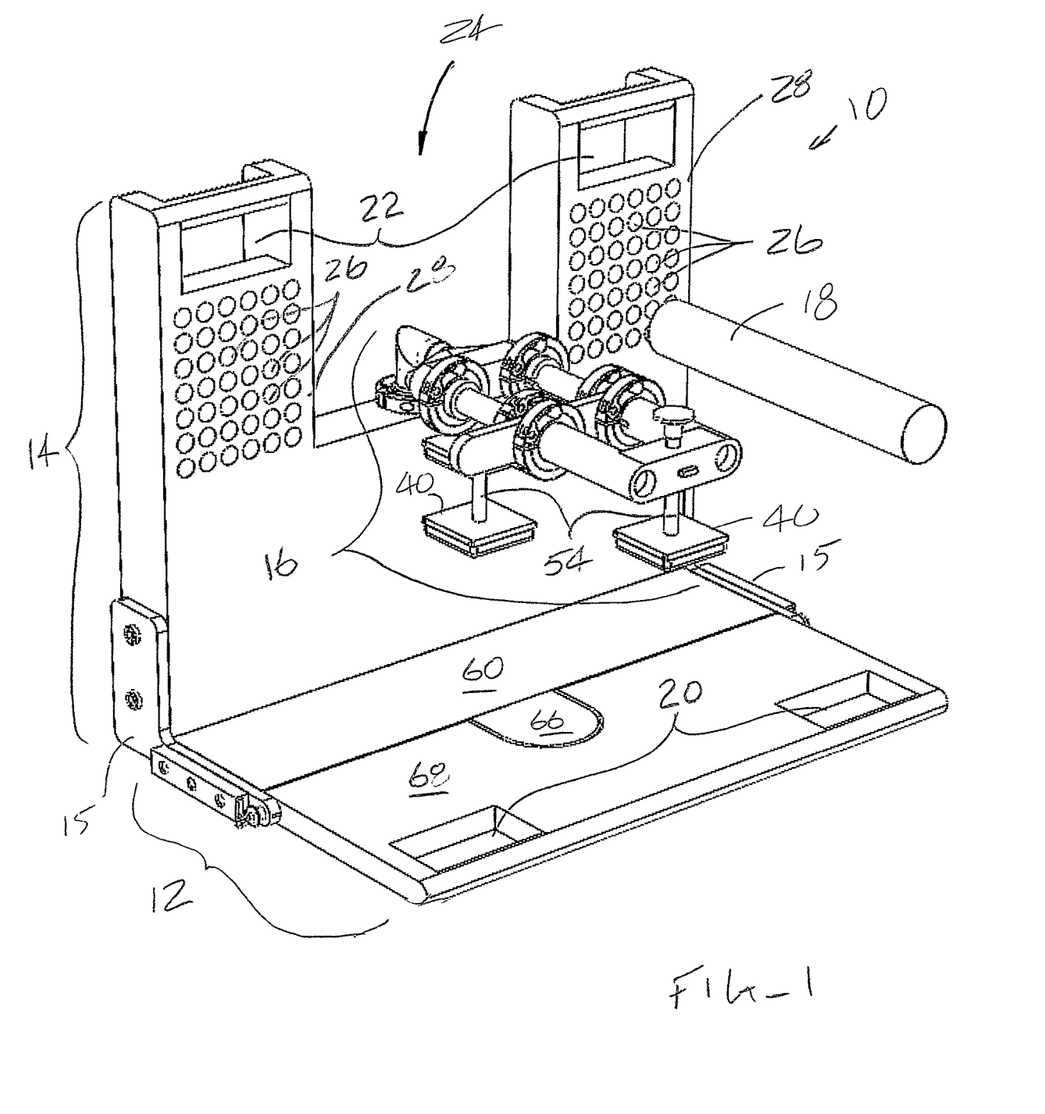
FIG. 1 is an isometric view of a patient positioning frame constructed in accordance with the principals of the present invention.
Figure 2:
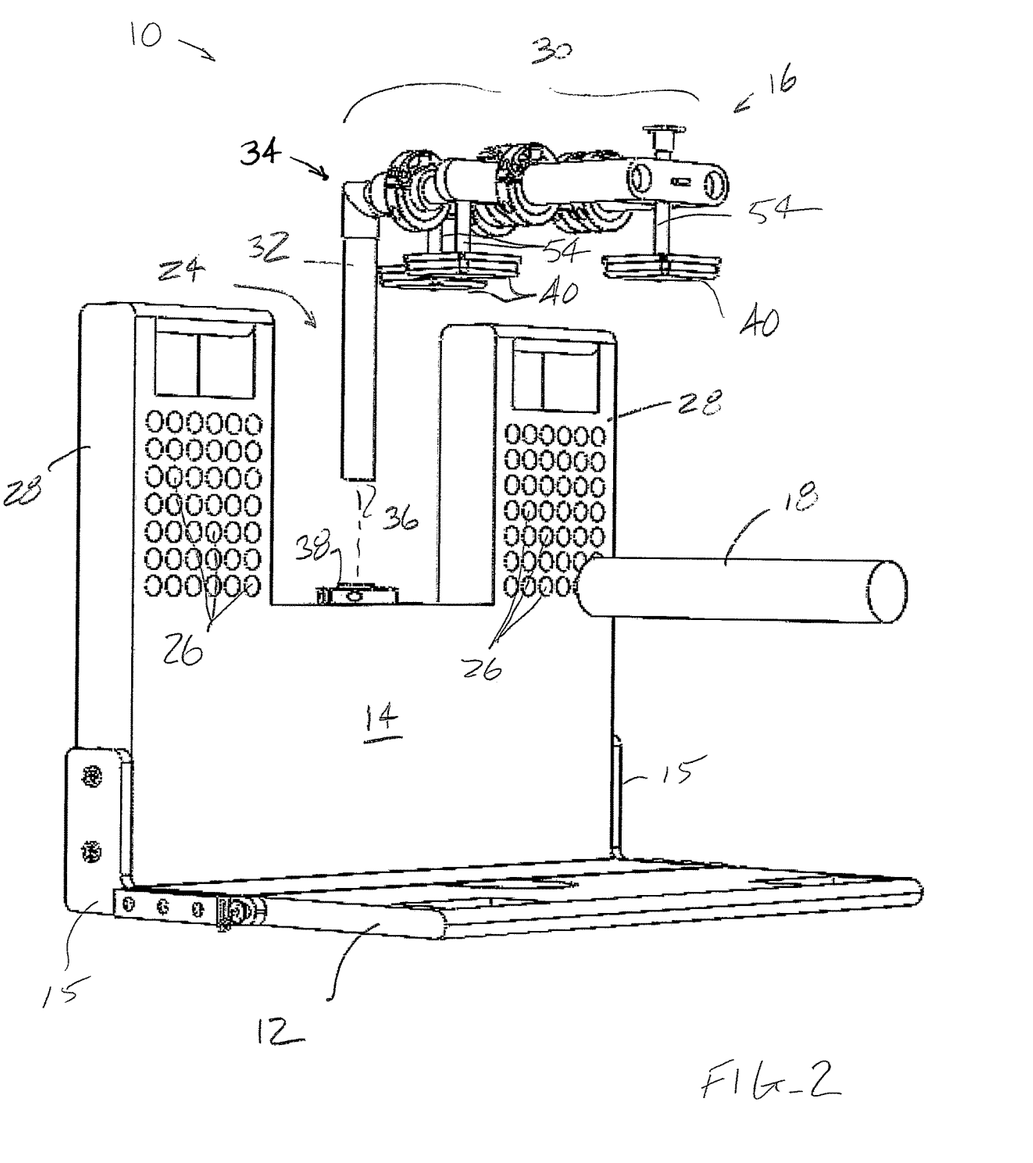
FIG. 2 is an isometric view of the patient positioning frame of FIG. 1 shown with an anterior restraint assembly removed from the remaining portions of the positioning frame.

Referring to FIGS. 1 and 2, a patient positioning frame 10 comprises a posterior support 12 and lateral support 14. The posterior support 12 and lateral support 14 are joined at a generally orthogonal angle, typically in the range from 80° to 100°, more usually being 90°, along common edges and are usually held together by braces 15 or other suitable structures. Alternatively, the posterior support and lateral support could be molded together or could be joined by adhesives or other means which can fix them together with sufficient strength so that they can be used to reposition patients as described in more detail herein below.

In addition to the posterior support 12 and the lateral support 14, the patient positioning frame 10 includes an anterior restraint assembly 16. The anterior restraint assembly 16 is attached to the lateral support 14 within a gap 24 formed between a pair of wings 28 which extend in a direction away from the posterior support 12. The patient positioning frame 10 further includes a chest bar 18 which is also removably attached to the lateral support 14, typically by placement in any one of an array, typically a planar array, of sockets 26 formed on each of the wings 28. Patient positioning frame 10 also includes handles so that the frame can be manually manipulated in order to reposition patients, as described in more detail below. For example, a pair of handles 20 may be formed in the posterior support 12 and a pair of handles 22 can be formed in the lateral support 14, typically with one handle 22 in each of the wings 28.

Figure 2A:
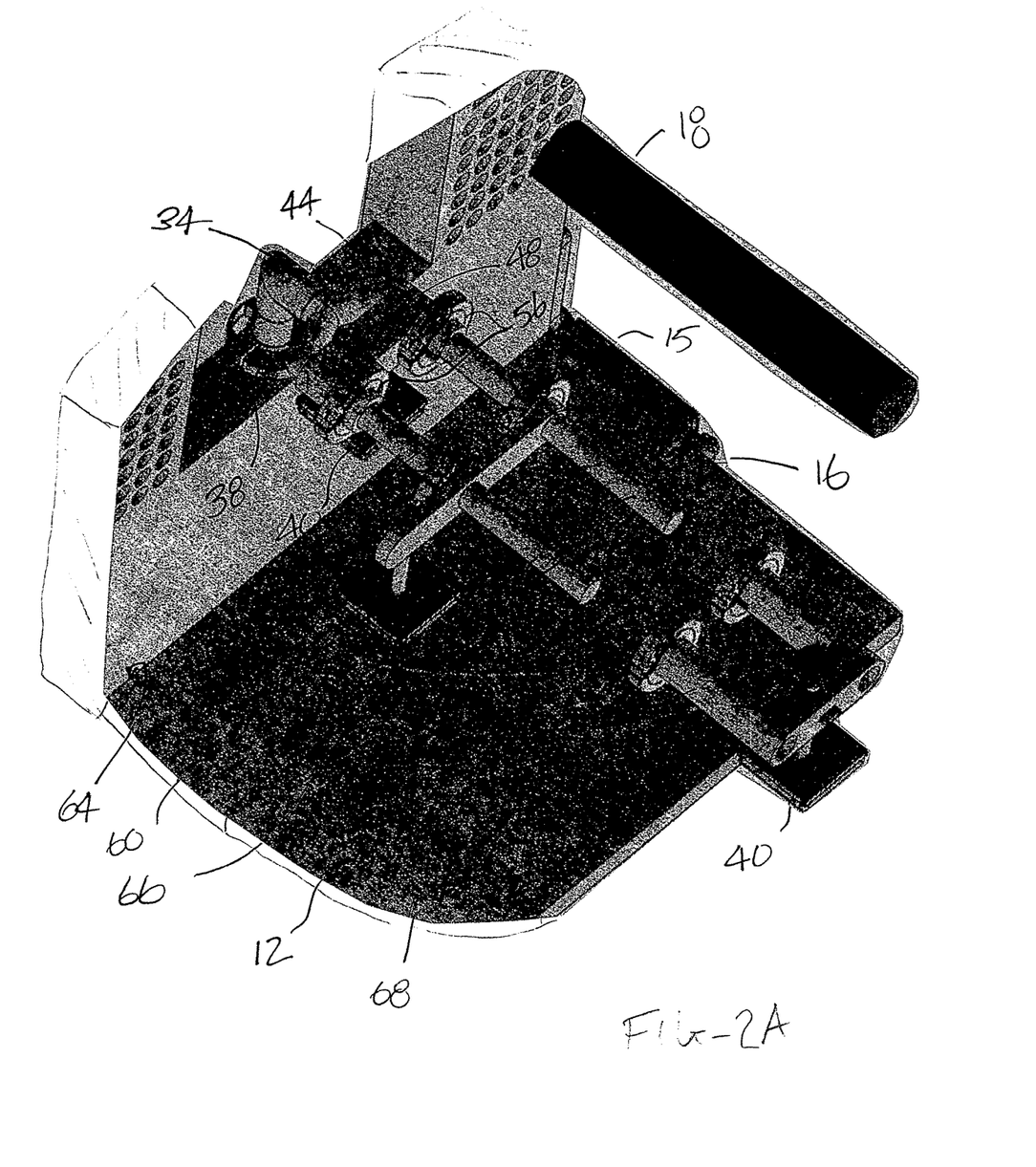
FIG. 2A is a detailed view of the anterior restraint assembly of the patient positioning frame of the present invention shown with portions of the frame broken away.

Referring now also to FIG. 2A, the anterior restraint assembly 16 includes a cantilevered section 30 and a post 32. The cantilevered section 30 is attached to the post at an anterior end 34 at a generally orthogonal angle, as previously defined. A posterior end 36 of the post 32 is removably received in a receptacle 38 formed in the lateral support 14 so that the anterior restraint assembly can be raised and lowered so that a distance between a lower surface of the anterior restraint assembly 16 and an upper surface of the posterior support 12 can be adjusted to accommodate patient's having different anatomies. Similarly, the chest bar 18 can be repositioned in different sockets 26 to accommodate both the patient anatomy and the positioning of the anterior restraint assembly.

A plurality of hip-engaging pads 40, typically three, depend from a lower side of the cantilevered support 30 so that the pads will engage the patient when the patient is lying on the posterior support 12, as described in more detail below. One hip-engaging pad is suspended from a first bracket 48, a second hip-engaging pad is attached to a second bracket 50, and a third hip-engaging pad is attached to a third bracket 52. The brackets 48, 50, and 52, in turn, are mounted on a pair of rods 46 which are attached to the anterior and 34 of the post 32 by a clevis 48. As best seen in FIG. 2A, each of the brackets can be axially translated along the rods 46 and locked in place using locking rings 56. In this way, the positions of the pads can be adjusted to accommodate different patient anatomies.

Figure 3A:
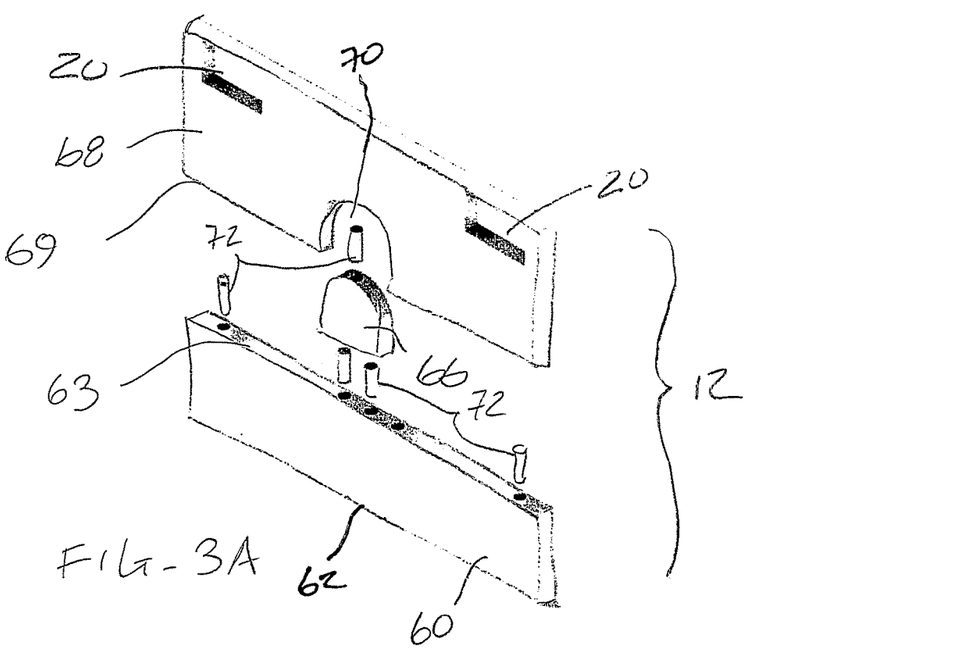
FIGS. 3A and 3B illustrate a posterior support of the patient positioning frame of the present invention in exploded views.
Figure 3B:
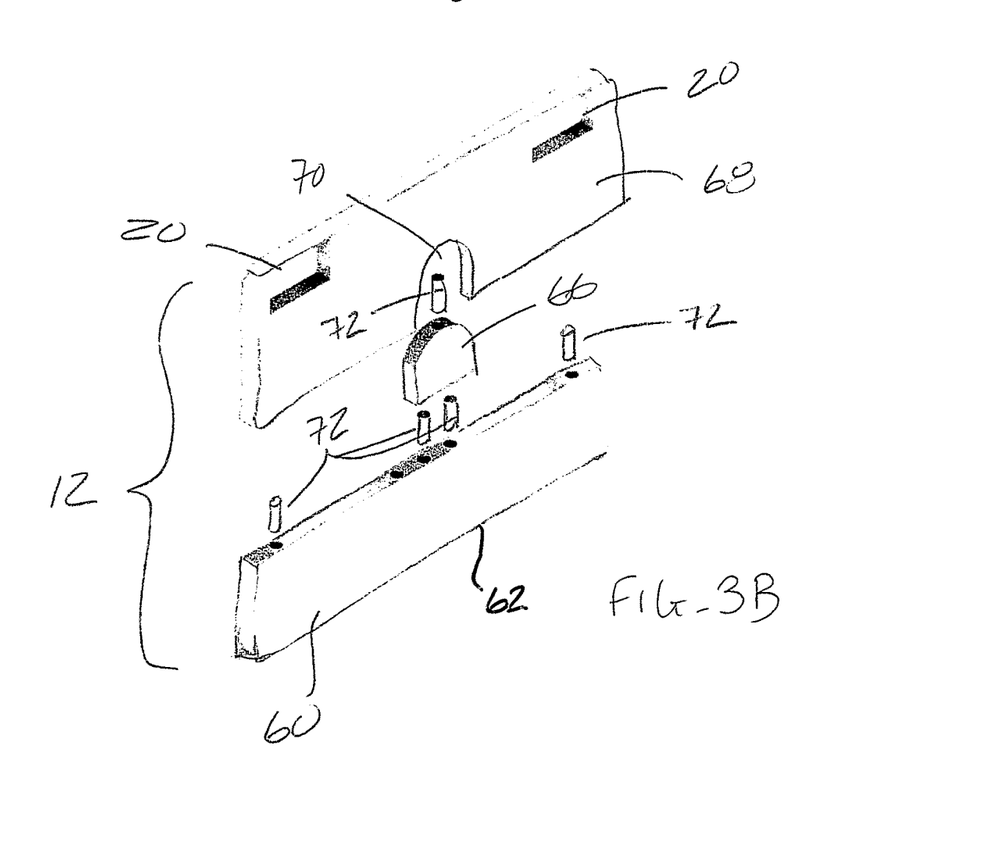

Referring now to FIGS. 3A and 3B, exemplary posterior supports 12 will comprise a backboard 60 having an inner edge 62 and an upper edge 63. The posterior support 12 will further include an extension panel 68 having a lower edge 69 which engages the upper edge 63 of the backboard 60.

The terms "lower" and "upper" are made with reference to the posterior support 12 as illustrated in FIGS. 3A and 3B, and it will be appreciated that the relative positions of these edges will change during use.

The posterior support 12 will typically also include a sacral post 66 which can be removably attached to the upper edge 63 of the backboard 60. The extension panel 68 will have a cut-out 70 which is sized and positioned to accommodate the sacral post 66 when the extension panel is in place and attached to the backboard. Conveniently, the backboard 60, extension panel 68, and sacral post 66 may be removably attached to each other using connecting pins 72.

The ability to adjust the axial position of the sacral post 66 along the length of the upper edge 63 of the backboard 60 is an advantage as it allows the position of the sacral post 66 to be adjusted depending on whether the patient is lying on his or her right side or left side. Similarly, the ability to place the chest bar 18 on either of the wings 28 of the lateral support 14 also allows the system to accommodate patients lying on either side. Similarly, the positions of the hip-engaging pads 40 on the anterior restraint assembly 16 can be moved and reversed in order to accommodate different patient positions and orientations. Additionally, it is noted that the lower edge 62 of the backboard 60 is joined to an inner edge 64 of the lateral support, as best seen in FIG. 2A.

Figure 4:
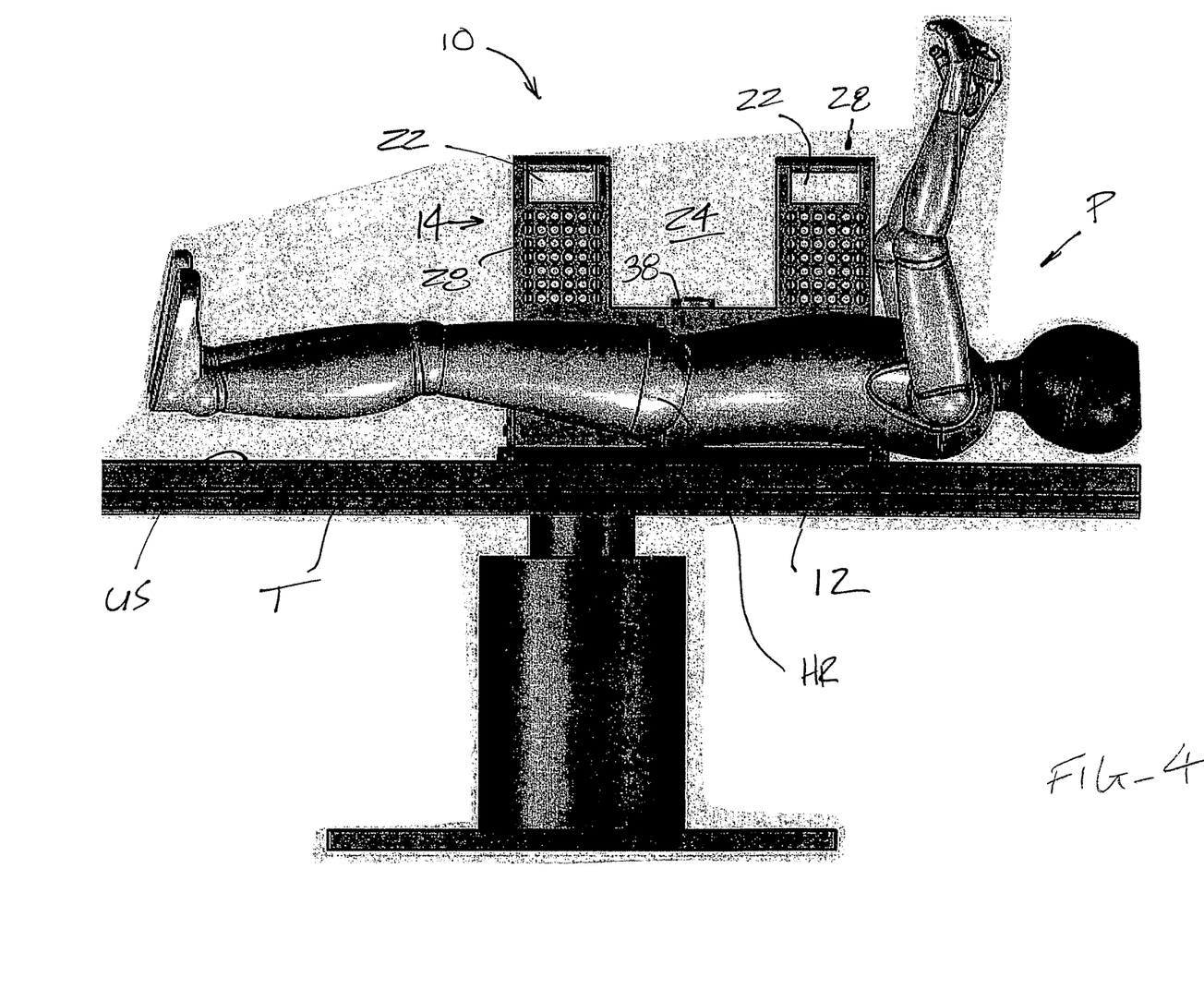
FIG. 4 illustrates the patient positioning frame of the present invention on an upper surface of the surgical table with a patient lying supine on the frame while it is on the table.

Referring now to FIG. 4, use of the patient positioning frame 10 for positioning a patient P on a surgical table T having an upper surface US will be described. The positioning frame 10 is initially placed on the upper surface US of the table T with the posterior support 12 lying on the upper surface in a generally horizontal plane. The lateral support 14, which is oriented orthogonally with respect to the posterior support 12, will generally be oriented in a vertical plane. The patient P lies in a supine orientation with his or her hip region HR generally aligned with the center of the gap 24 and receptacle 38 of the lateral support 14. The patient is oriented with his or her head in a rightward direction, as shown in FIG. 4, and the patient will be in this orientation if it is desired to operate on the patient's left hip region HR. If it is desired to operate on the patient's right hip region, the patient would lie in an orientation with his or her head in the leftward direction as shown FIG. 4.

Figure 5:
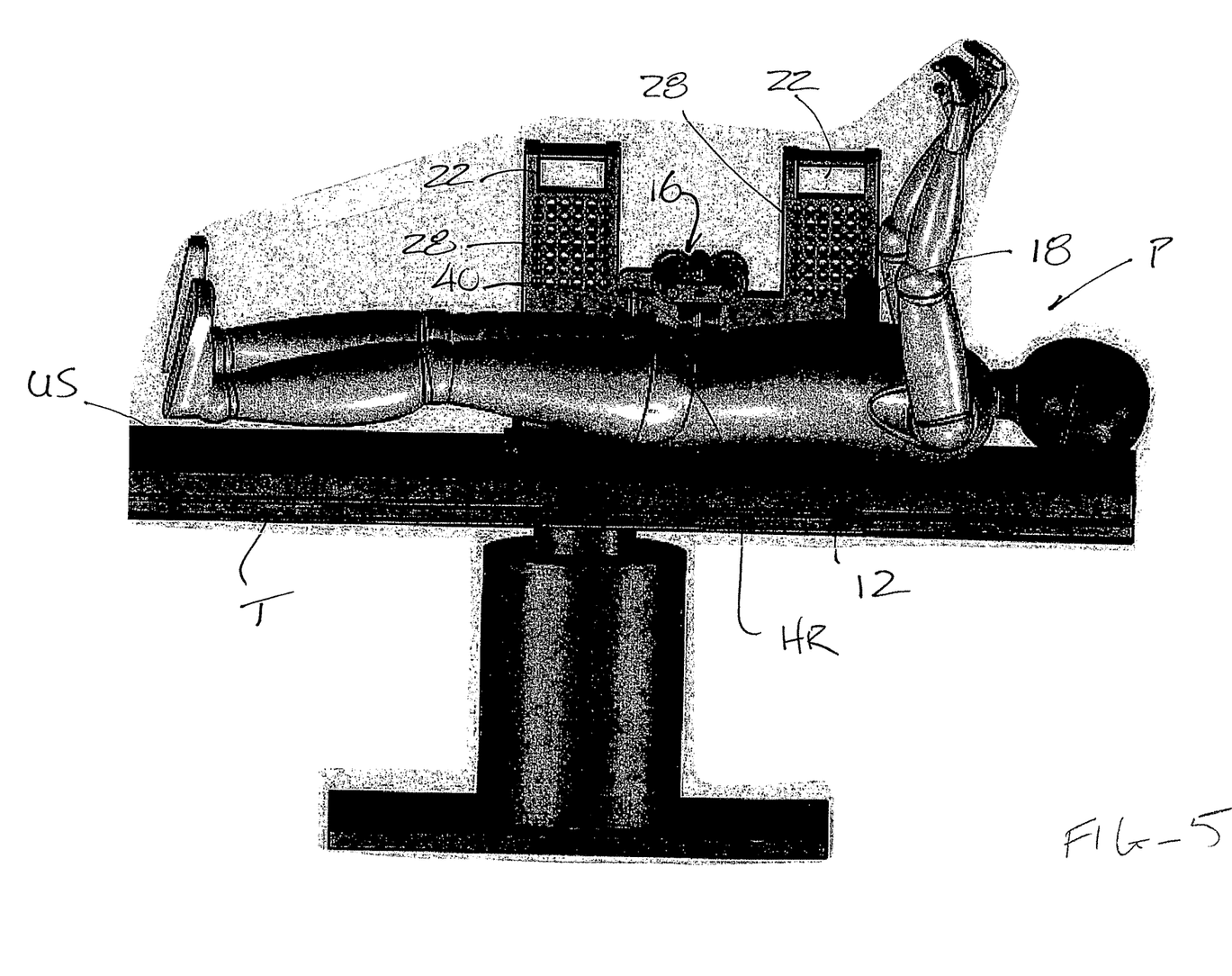
FIG. 5 illustrates the patient as in FIG. 4 with an anterior restraint assembly having been secured to the patient positioning frame to hold the patient in place with respect to the frame.

Referring now to FIG. 5, after the patient P has assumed the supine position, as shown in FIG. 4, the anterior restraint assembly 16 will be positioned so that the individual hip-engaging pads 40 engage the hip region HR of the patient. The positions of the individual hip-engaging pads 40 may be adjusted in order to properly accommodate the anatomy of the individual patient while providing sufficient restraining or securing force to hold the patient's hip region HR immobile relative to the patient positioning frame 10 during subsequent patient reorientation, as described in more detail below. Additionally, the chest bar 18 will be placed to engage the patient's chest to further restrain movement of the patient. Although not illustrated, pillows, padding, and other conventional patient positioning items will be used to both stabilize the patient's position and to make the patient more comfortable.

Figure 5A:
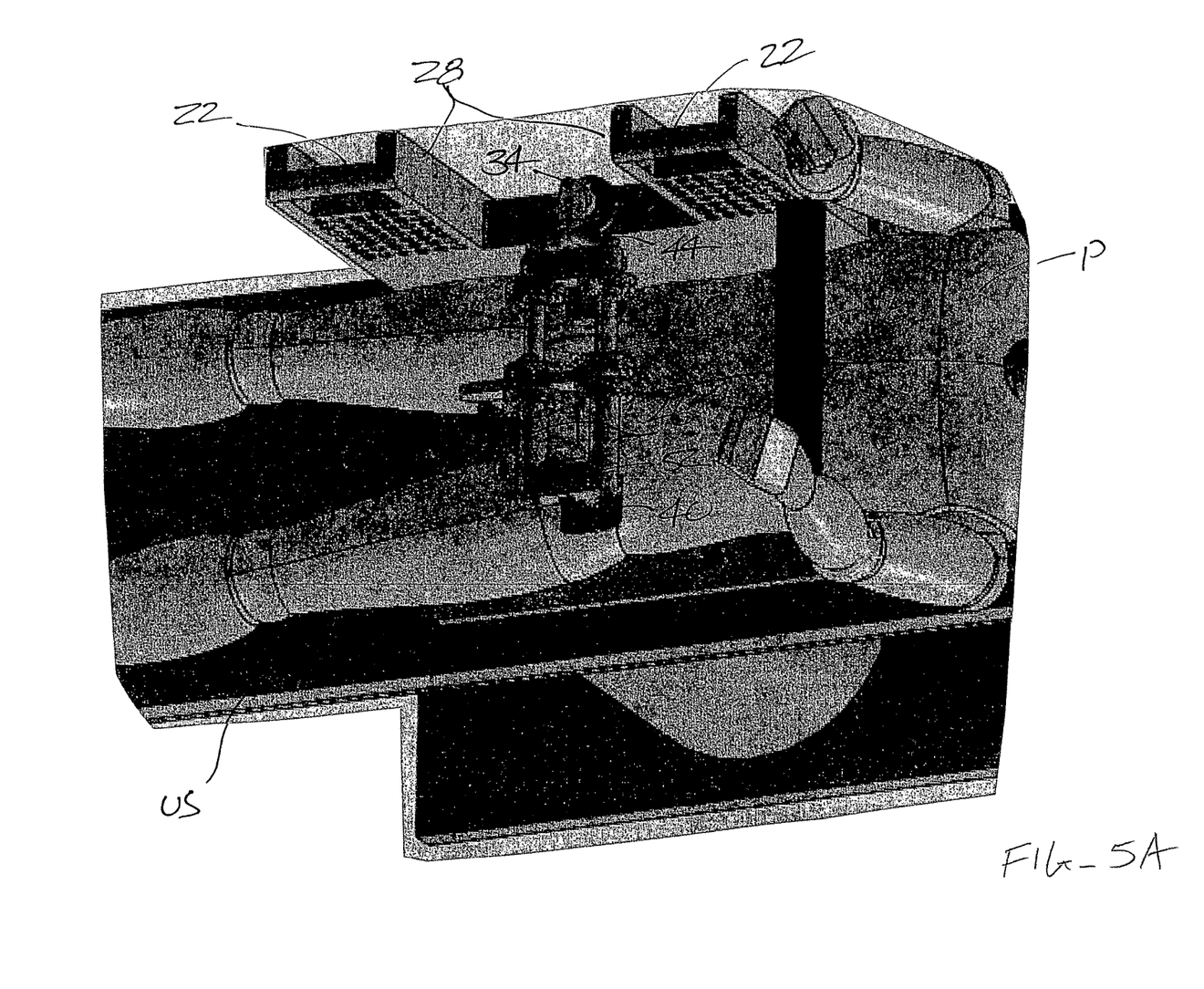
FIG. 5A is a detailed view illustrating the anterior restraint assembly as it engages a hip region of the patient while lying supine on the positioning frame and prior to turning of the frame.

Proper positioning of the individual hip pads 40 is best observed in FIG. 5A where the patient is in the position illustrated in FIG. 5.

Figure 6:
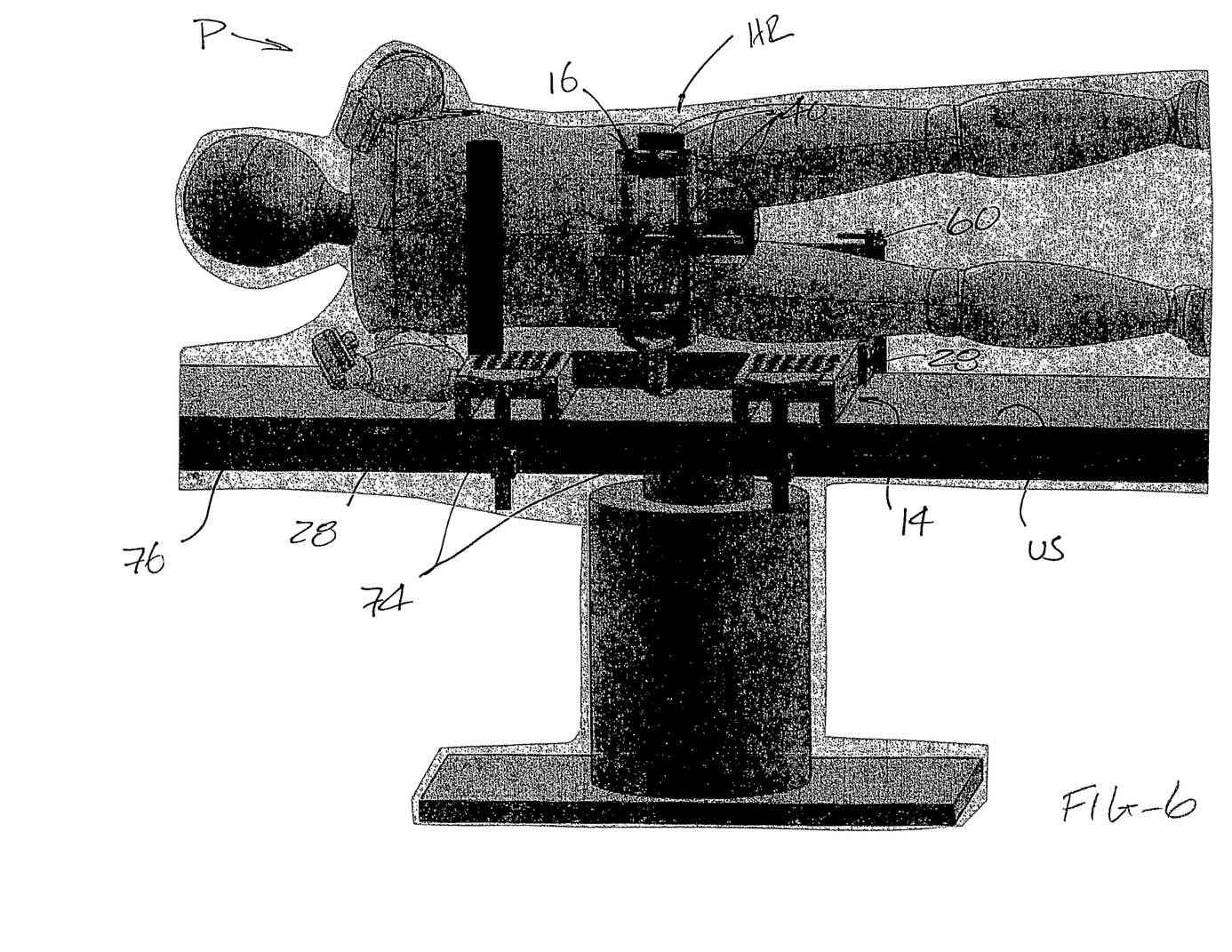
FIG. 6 is an anterior view of the patient on the patient positioning frame after the frame and the patient have been turned on top of a surgical table.
Figure 7:
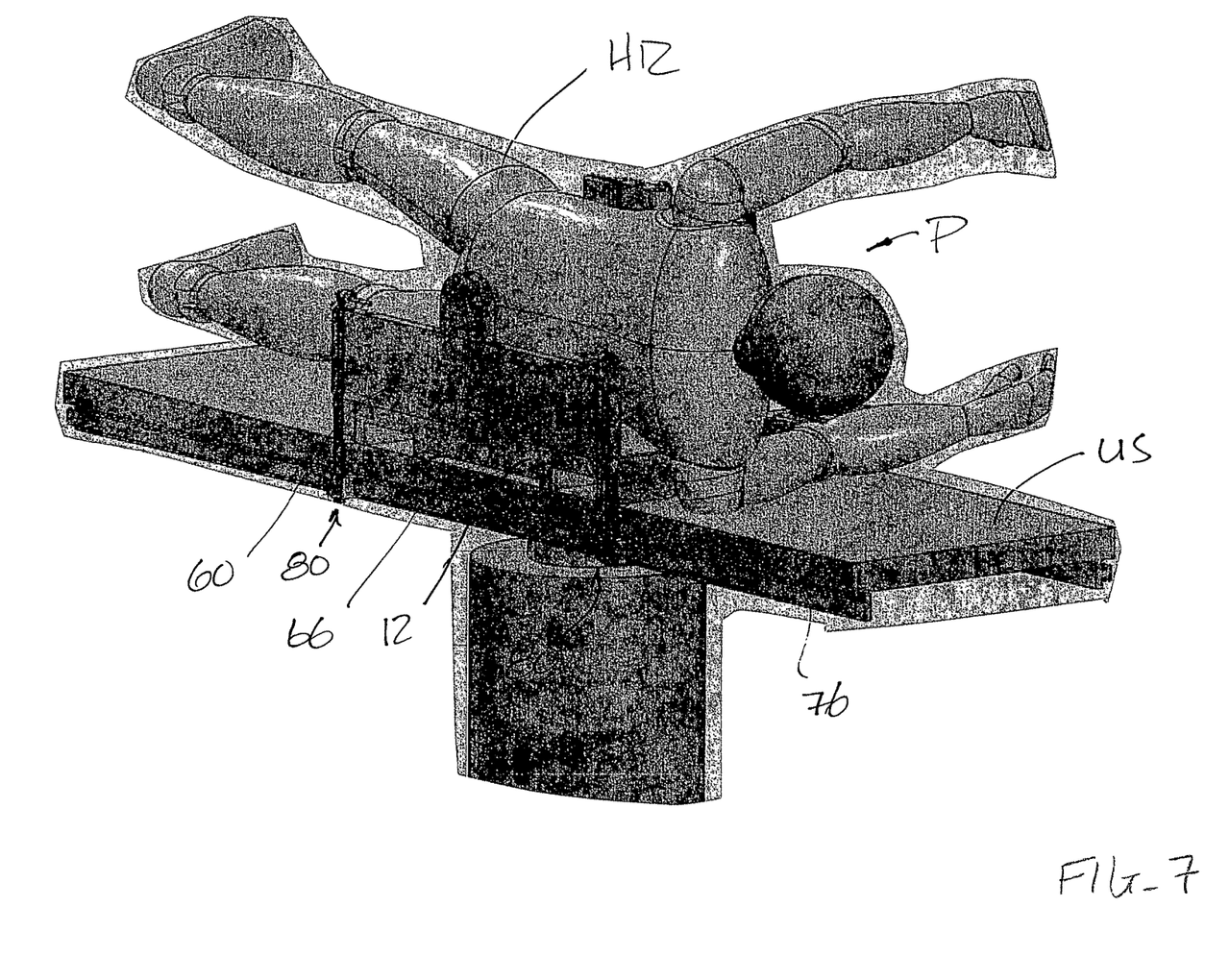
FIG. 7 is a posterior view of the patient in a position similar to that of FIG. 6.

Once the patient has been properly positioned on the patient positioning frame 10, and the anterior restraint assembly 16 and chest bar 18 properly adjusted to restrain and stabilize the patient, the patient positioning frame 10 with the patient restrained therein will be turned or rotated by 90° so that the patient is lying on his or her right side with the left side exposed for the hip surgery, as shown in FIGS. 6 and 7. After the patient has been turned and reoriented, the extension panel 68 of the lateral support 14 may be removed to better expose the left side of the hip region HR for subsequent surgery. As shown in FIG. 7, the sacral post 66 will remain in place to engage the patient's sacrum to maintain the immobility and stabilization of the patient during the procedure. As noted previously, if the patient were lying on the patient's opposite side, the position of the sacral post 66 would have been moved to accommodate the patient's anatomy.

After the patient has been turned and properly oriented, the patient positioning frame may be secured to the surgical table T using conventional brackets 80 which are attached to a rail 76 on the surgical table. Additionally, C-shaped clamps 74 may be used on the opposite side of the table to secure the wings 28 to the table.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventor expects skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A patient positioning frame comprising:
   a posterior support;
   a lateral support attached non-adjustably and orthogonally to the posterior support; and
   an anterior restraint adjustably coupled to the lateral support, wherein the anterior restraint is configured to engage the pelvis of a patient to immobilize the hip region relative to the posterior and lateral supports;
   wherein the posterior support is configured to engage against the back of the patient lying in a supine position while the posterior support is in a horizontal position on a surgical table and, after adjusting the anterior restraint to immobilize the patient's hip region relative to the patient positioning frame, the patient positioning frame is configured to be simultaneously turned with the patient so that the lateral support lies horizontally on the surgical table and the posterior support is oriented vertically to place the patient on his or her side to expose the hip or other target surgical region.

2. A patient positioning frame as in claim 1, wherein the posterior support comprises (1) a backboard having an inner edge fixed to an inner edge of the lateral support and (2) an extension having an inner edge removably secured to an outer edge of the backboard.

3. A patient positioning frame as in claim 2, wherein the posterior support further comprises (3) a sacral post extending from the outer edge of the backboard, said sacral post being positioned to engage a patient's sacrum when the patient's back is against the posterior support and the patient's side is against the lateral support.

4. A patient positioning frame as in claim 1, wherein the sacral post is configured to be axially repositioned along the outer edge of the backboard to accommodate different patient anatomies.

5. A patient positioning frame as in claim 1, wherein the posterior support has handles to allow manual repositioning of the patient positioning frame.

6. A patient positioning frame as in claim 1, wherein the lateral support has handles to allow manual repositioning of the patient positioning frame.

7. A patient positioning frame as in claim 6, wherein the handles in the lateral support have a gap therebetween and wherein the anterior restraint is coupled to the lateral support in the gap.

8. A patient positioning frame as in claim 1, wherein the anterior restraint comprises (1) a post having an anterior end and a posterior end and (2) a cantilevered section extending laterally from the anterior end of the post, wherein the posterior end of the post is translatably attached to the lateral support so that a spacing between the cantilevered section and the posterior support can be adjusted to accommodate different patient anatomies.

9. A patient positioning frame as in claim 8, wherein the anterior restraint comprises (3) a plurality of hip-engaging pads which extend in a posterior direction to engage a hip region of the patient when the patient is lying supine on the posterior support with the cantilevered section extending over the hip region.

10. A patient positioning frame as in claim 9, wherein at least some of the plurality of hip-engaging pads are configured to be adjustably positioned in an anterior-posterior direction relative to the cantilevered section.

11. A patient positioning frame as in claim 1, wherein the anterior restraint further comprises a chest bar extending laterally from the lateral support to lie over the patient's chest when patient is lying supine on the posterior support.

12. A patient positioning frame as in claim 11, wherein the chest bar is repositionable on the lateral support to accommodate different patient anatomies.

13. A method for positioning a patient for a surgical procedure, said method comprising:
providing a patient positioning frame including a posterior support attached non-adjustably and orthogonally to a lateral support;
placing the posterior support of the patient positioning frame in a first orientation horizontally on an upper surface of a surgical table so that the lateral support extends vertically upwardly from the upper surface;
securing the patient in a supine position over the posterior support with a side of the patient adjacent the lateral support while the patient positioning frame remains in the first orientation; and
simultaneously turning the patient positioning frame and the patient to a second orientation with the lateral support lying horizontally on the upper surface of the surgical table and the posterior support extending vertically upwardly from the upper surface;
wherein a side of the patient becomes exposed for a surgical procedure.

14. The method for positioning a patient of claim 13, further comprising performing surgery on the patient's hip region.

15. The method for positioning a patient of claim 14, wherein the surgery comprises hip replacement.

16. The method for positioning a patient of claim 13, wherein securing the patient in a supine position comprises engaging an anterior restraint against a hip region of the patient.

17. The method for positioning a patient of claim 16, wherein the anterior restraint is adjustably coupled to the lateral support and wherein engaging comprises repositioning the anterior restraint relative to the lateral support.

18. The method for positioning a patient of claim 17, wherein repositioning the anterior restraint relative to the lateral support comprises repositioning a plurality of hip-engaging pads which extend in a posterior direction to engage a hip region of the patient.

19. The method for positioning a patient of claim 13, further comprising removing an upper portion of the posterior support after the patient and the patient positioning frame have been turned to expose a surgical target region.

20. The method for positioning a patient of claim 19, wherein removing the upper portion of the posterior support leaves a sacral post extending upwardly from the remaining portion of the posterior support to engage the patient's sacrum.

21. The method for positioning a patient of claim 20, further comprising repositioning the sacral post along an edge of the posterior support before or after the upper portion has been removed.

22. The method for positioning a patient of claim 14, wherein simultaneously turning the patient positioning frame and the patient comprises manually grasping handles formed on the patient positioning frame.

23. The method for positioning a patient of claim 14, further comprising reconfiguring the patient positioning frame to accommodate a right side or a left side of the patient prior to securing the patient to the patient positioning frame.

* * * * *